United States Patent
Hiles et al.

(10) Patent No.: US 10,512,463 B2
(45) Date of Patent: Dec. 24, 2019

(54) MEDICAL DEVICES AND METHODS USEFUL FOR APPLYING BOLSTER MATERIAL

(71) Applicant: Cook Biotech Incorporated, West Lafayette, IN (US)

(72) Inventors: Michael C. Hiles, West Lafayette, IN (US); Umesh H. Patel, West Lafayette, IN (US); Bhavin Shah, West Lafayette, IN (US); Chad S. McAlexander, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 348 days.

(21) Appl. No.: 14/873,335

(22) Filed: Oct. 2, 2015

(65) Prior Publication Data

US 2016/0220250 A1     Aug. 4, 2016

Related U.S. Application Data

(63) Continuation of application No. 12/110,006, filed on Apr. 25, 2008, now Pat. No. 9,186,140, which is a
(Continued)

(51) Int. Cl.
*A61B 17/08* (2006.01)
*A61B 17/072* (2006.01)
(Continued)

(52) U.S. Cl.
CPC .... *A61B 17/07292* (2013.01); *A61B 17/0643* (2013.01); *A61B 17/0644* (2013.01);
(Continued)

(58) Field of Classification Search
CPC ............ A61B 17/072; A61B 17/07207; A61B 17/07292; A61B 2017/07214
See application file for complete search history.

(56) References Cited

U.S. PATENT DOCUMENTS

| 3,800,792 A | 4/1974 | McKnight et al. |
| 4,902,508 A | 2/1990 | Badylak et al. |

(Continued)

FOREIGN PATENT DOCUMENTS

| EP | 0 090 997 | 10/1983 |
| EP | 0090997 | 10/1983 |

(Continued)

OTHER PUBLICATIONS

Crocker, H. et al., "The Assessment of Bovine Pericardial Stripsi in the Reduction of Air Leak Following Lung Volume Reduction Surgery," The Thoracic Societyof Australia & New Zealand 1998 Annual Scientific Meeting—Adelaid, Mar. 15-18.

(Continued)

*Primary Examiner* — Todd J Scherbel
(74) *Attorney, Agent, or Firm* — Woodard, Emhardt, Henry, Reeves & Wagner, LLP

(57) ABSTRACT

Described are medical devices useful for applying a bolster material to a surgical fastening device such as a stapler, and related methods of manufacture and use. The devices include an applicator element for receipt between arms of the stapler, and a bolster material, desirably a remodelable extracellular matrix material, coupled to the applicator element. In certain embodiments, the bolster material is held by the applicator element, for example having at least a portion looped around or received through or over a portion of the applicator element. Also described are unique implantable materials including coatings of dried, reversible adhesive.

20 Claims, 13 Drawing Sheets

Related U.S. Application Data continuation of application No. 11/060,078, filed on Feb. 17, 2005, now Pat. No. 8,920,443.

(60) Provisional application No. 60/545,513, filed on Feb. 17, 2004.

(51) Int. Cl.
  *A61B 17/064* (2006.01)
  *A61B 17/00* (2006.01)
  *A61B 90/00* (2016.01)
  *A61B 50/20* (2016.01)

(52) U.S. Cl.
  CPC ...... *A61B 17/072* (2013.01); *A61B 17/07207* (2013.01); *A61B 17/00491* (2013.01); *A61B 50/20* (2016.02); *A61B 2017/00884* (2013.01); *A61B 2090/037* (2016.02)

(56) References Cited

U.S. PATENT DOCUMENTS

| | | | |
|---|---|---|---|
| 4,950,699 A | 8/1990 | Holman | |
| 4,956,178 A | 9/1990 | Badylak et al. | |
| 5,214,093 A | 5/1993 | Nell et al. | |
| 5,281,422 A | 1/1994 | Badylak et al. | |
| 5,503,638 A | 4/1996 | Cooper et al. | |
| 5,549,628 A | 8/1996 | Cooper et al. | |
| 5,554,389 A | 9/1996 | Badylak et al. | |
| 5,575,803 A | 11/1996 | Cooper et al. | |
| 5,702,720 A | 12/1997 | Effing et al. | |
| 5,752,965 A | 5/1998 | Francis et al. | |
| 5,755,791 A | 5/1998 | Whitson et al. | |
| 5,902,312 A | 5/1999 | Frater et al. | |
| 5,908,427 A | 6/1999 | McKean et al. | |
| 5,955,110 A | 9/1999 | Patel et al. | |
| 5,964,774 A | 10/1999 | McKean et al. | |
| 5,993,844 A | 11/1999 | Abraham et al. | |
| 5,997,575 A | 12/1999 | Whitson et al. | |
| 6,099,551 A | 8/2000 | Gabbay | |
| 6,099,567 A | 8/2000 | Badylak et al. | |
| 6,206,931 B1 | 3/2001 | Cook et al. | |
| 6,325,810 B1 | 12/2001 | Hamilton et al. | |
| 6,329,564 B1 | 12/2001 | Lebner | |
| 6,428,561 B1 | 8/2002 | Johansson-Ruden et al. | |
| 6,475,232 B1 | 11/2002 | Babbs et al. | |
| 6,503,257 B2 | 1/2003 | Grant et al. | |
| 6,544,642 B2 | 4/2003 | Cinelli et al. | |
| 6,638,285 B2 | 10/2003 | Gabbay | |
| 6,704,210 B1 | 3/2004 | Myers | |
| 6,939,358 B2 | 9/2005 | Palacios et al. | |
| 7,547,312 B2 | 6/2009 | Bauman et al. | |
| 8,920,443 B2 * | 12/2014 | Hiles .................. | A61B 17/072 227/176.1 |
| 8,920,444 B2 * | 12/2014 | Hiles .................. | A61B 17/072 227/176.1 |
| 9,186,140 B2 * | 11/2015 | Hiles .................. | A61B 17/072 |
| 2002/0086423 A1 | 7/2002 | Takezawa et al. | |
| 2003/0073979 A1 | 4/2003 | Naimark et al. | |
| 2003/0120284 A1 | 6/2003 | Palacios et al. | |
| 2003/0149406 A1 | 8/2003 | Martineau et al. | |
| 2005/0059997 A1 | 3/2005 | Bauman et al. | |
| 2005/0070929 A1 * | 3/2005 | Dalessandro .... | A61B 17/07207 606/151 |
| 2005/0184121 A1 | 8/2005 | Heinrich | |
| 2005/0228446 A1 | 10/2005 | Mooradian et al. | |
| 2007/0027472 A1 | 2/2007 | Hiles et al. | |

FOREIGN PATENT DOCUMENTS

| | | |
|---|---|---|
| EP | 0 781 564 | 7/1997 |
| EP | 0781564 | 7/1997 |
| EP | 1 129 665 | 5/2001 |
| EP | 1129665 | 5/2001 |
| EP | 1 520 525 | 4/2005 |
| EP | 1520525 | 4/2005 |
| ES | 2 024 769 | 3/1992 |
| ES | 2024769 | 3/1992 |
| GB | 892 633 A | 3/1962 |
| GB | 892633 | 3/1962 |
| WO | WO 1996/07356 | 3/1996 |
| WO | WO 1997/01989 | 1/1997 |
| WO | WO 1998/17180 | 4/1998 |
| WO | WO 1999/02090 | 1/1999 |
| WO | WO 2002/082975 | 10/2002 |
| WO | WO 2003/053254 | 7/2003 |
| WO | WO 2003/088844 | 10/2003 |

OTHER PUBLICATIONS

Miller, J. et al., "A Comparative Study of Buttressed vs Non-Buttressed Staple Line in Pulmonary Resections," The Emory Clinic, Atlanta, Georgia STSA 46th Meeting.

* cited by examiner

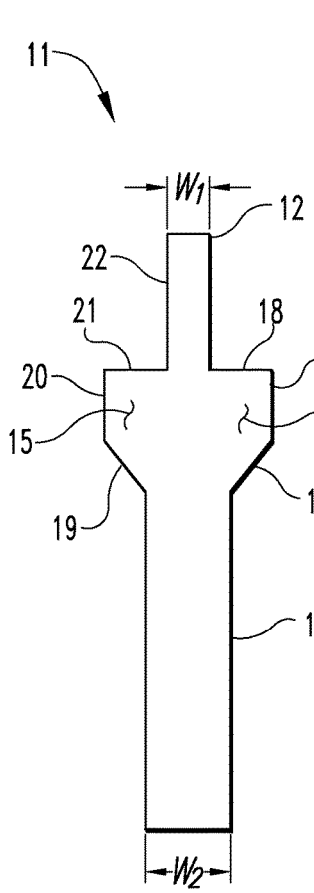
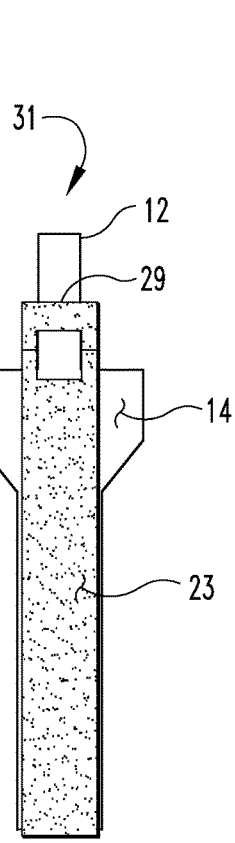
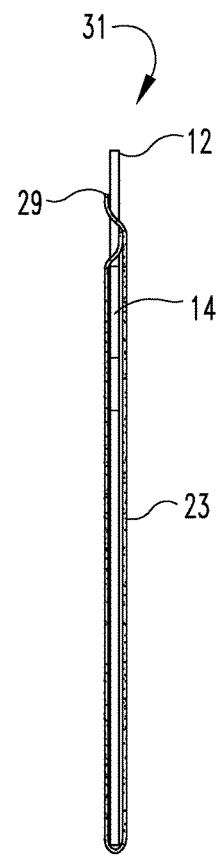
Fig. 1  Fig. 3  Fig. 4
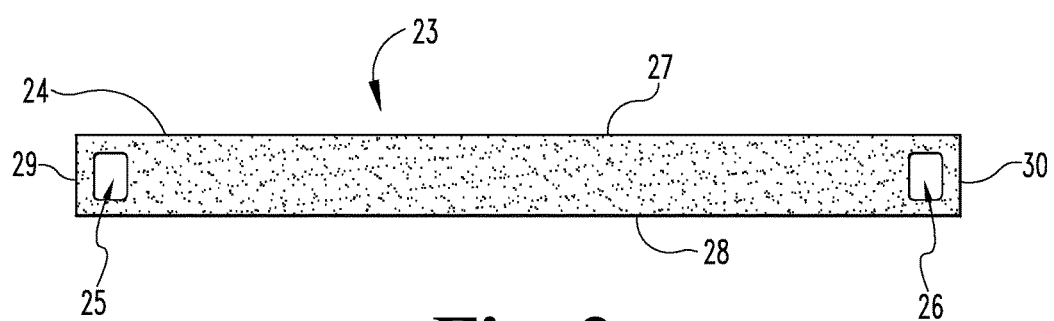
Fig. 2

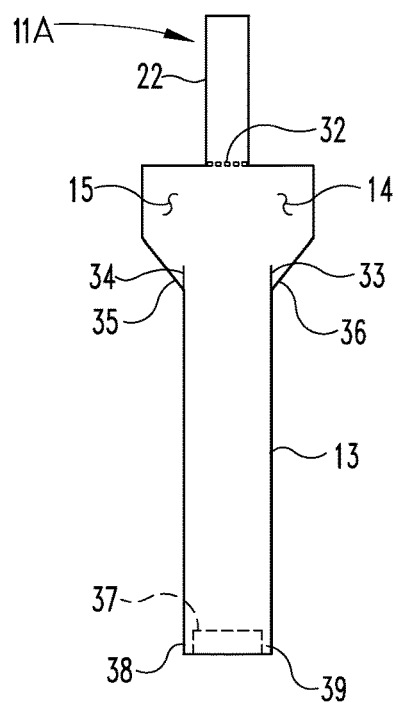
Fig. 5
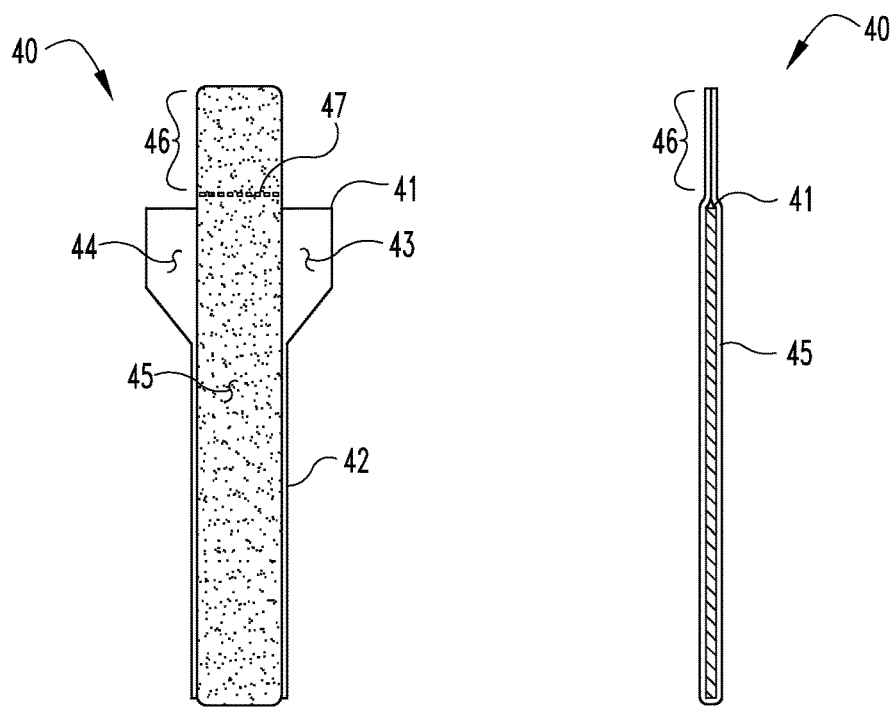
Fig. 6  Fig. 7

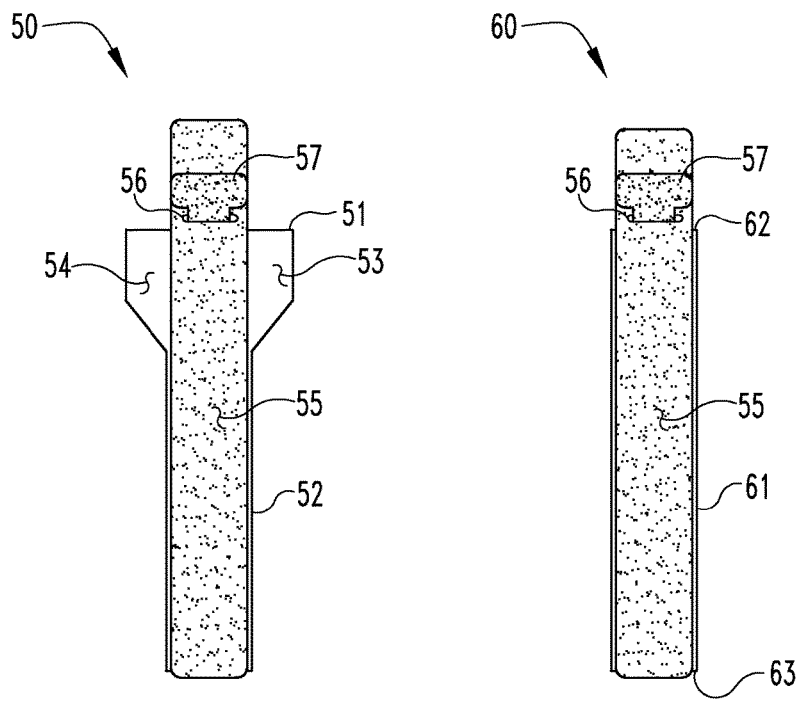
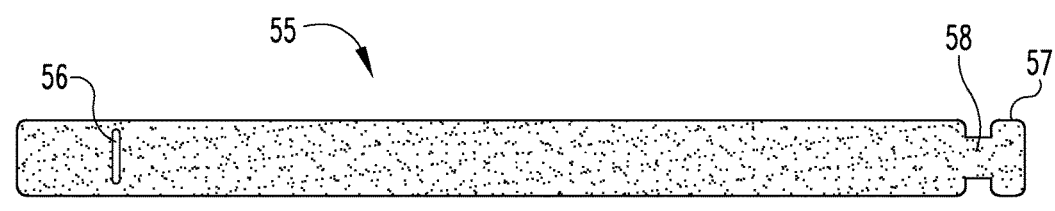

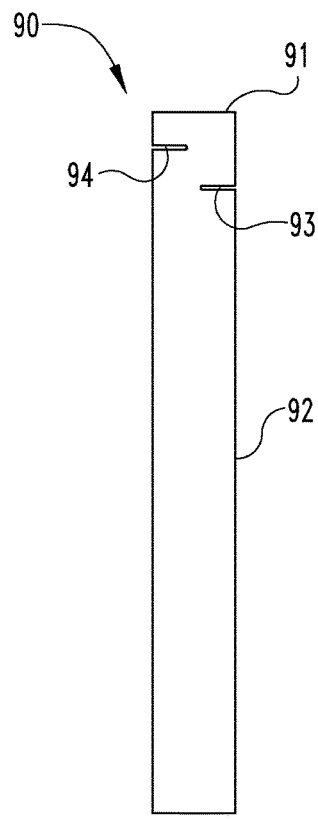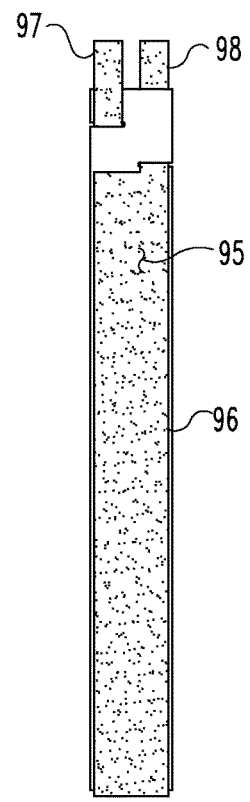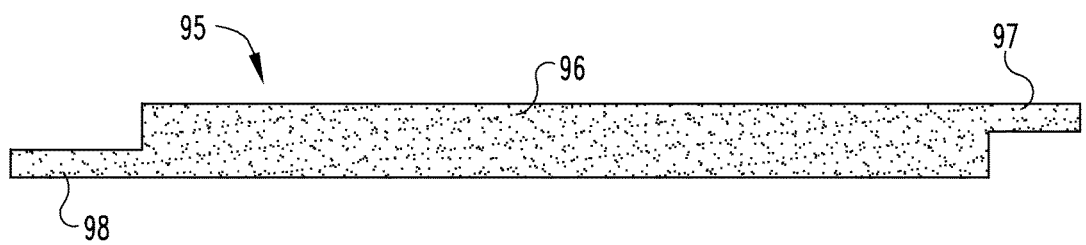
Fig. 15  Fig. 17
Fig. 16

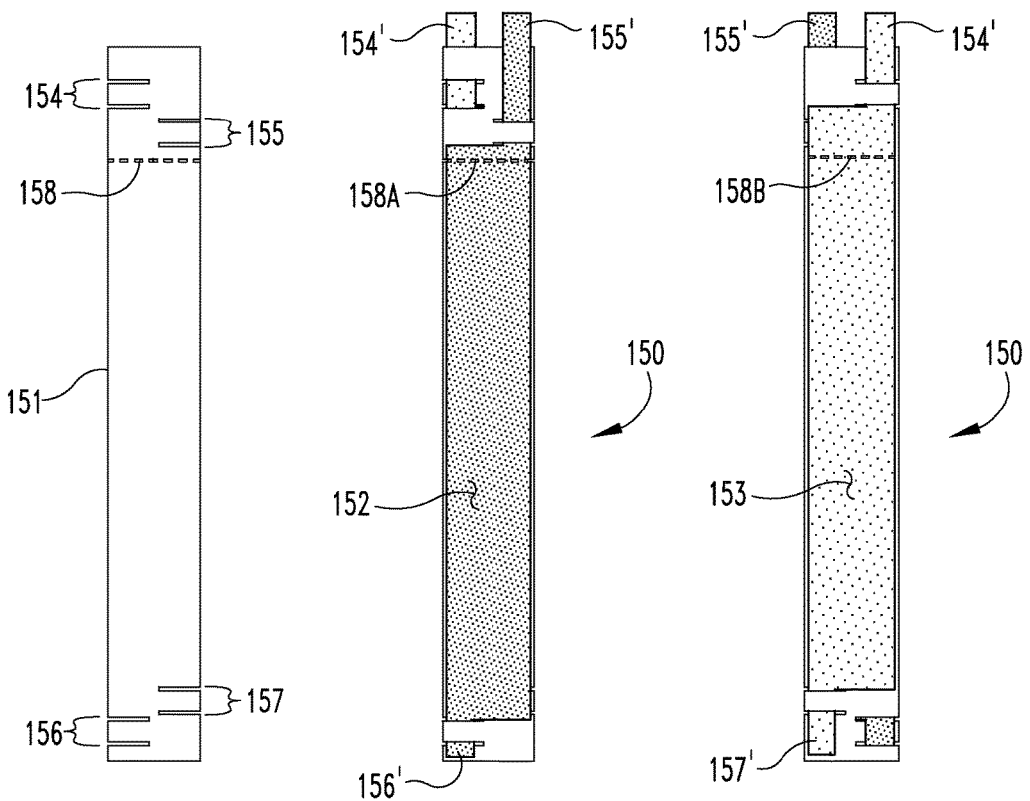
Fig. 28  Fig. 29A  Fig. 29B
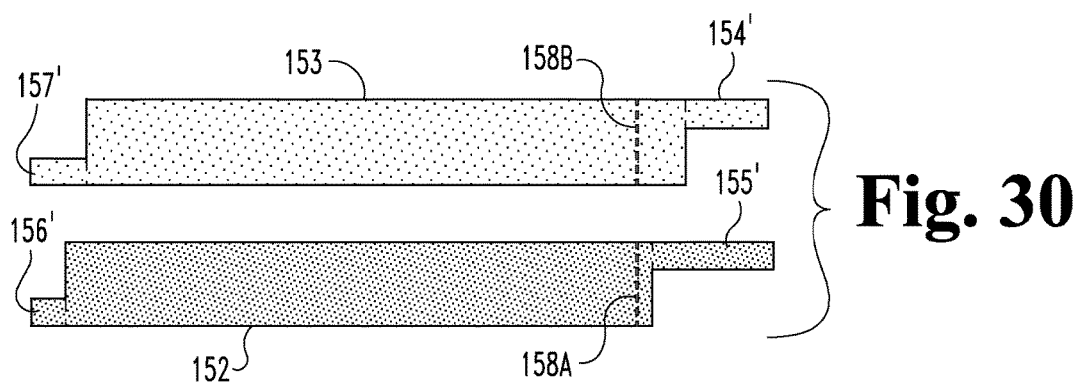
Fig. 30

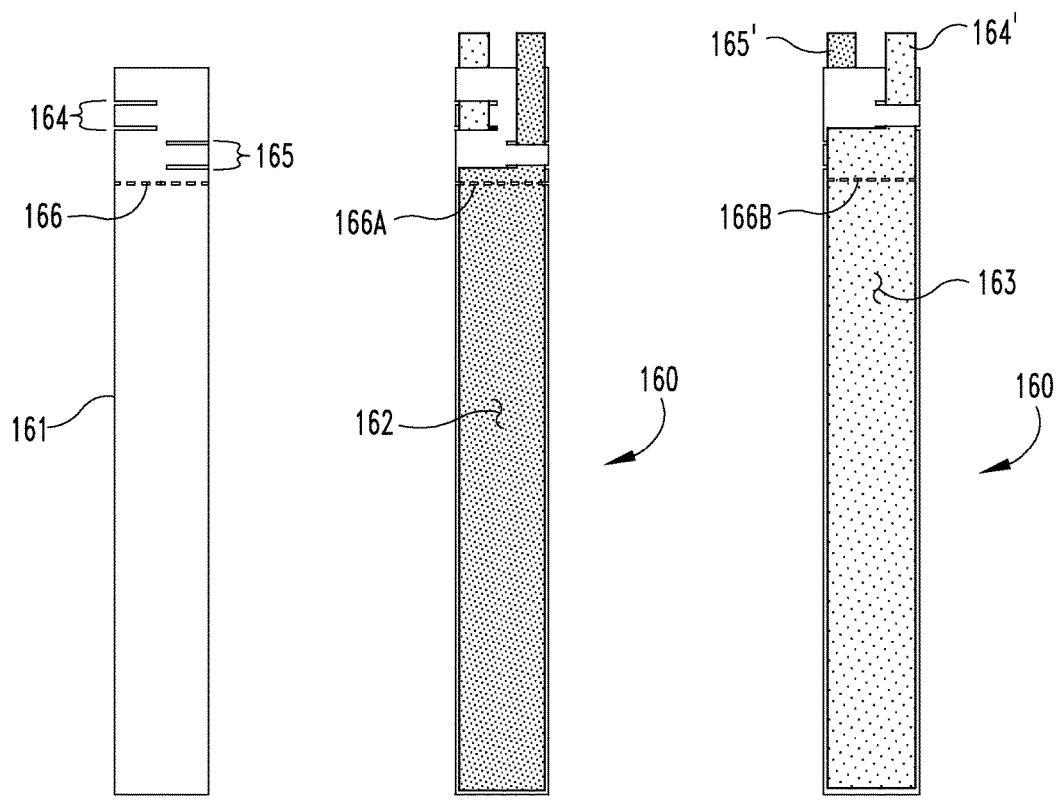
Fig. 31  Fig. 32A  Fig. 32B
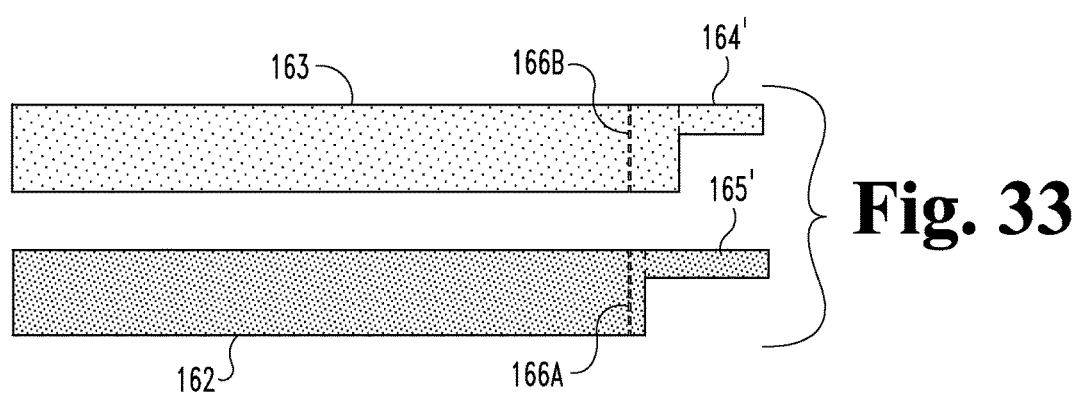
Fig. 33

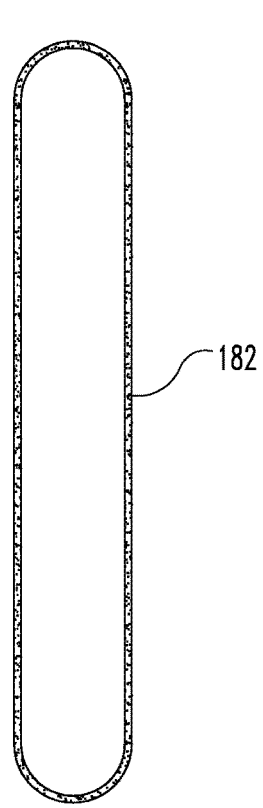
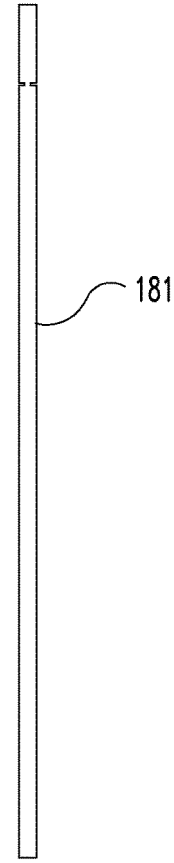
Fig. 36  Fig. 37
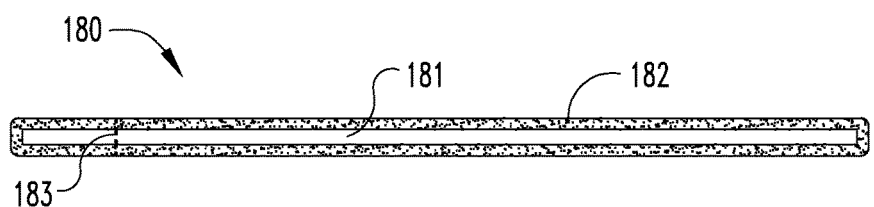
Fig. 38A
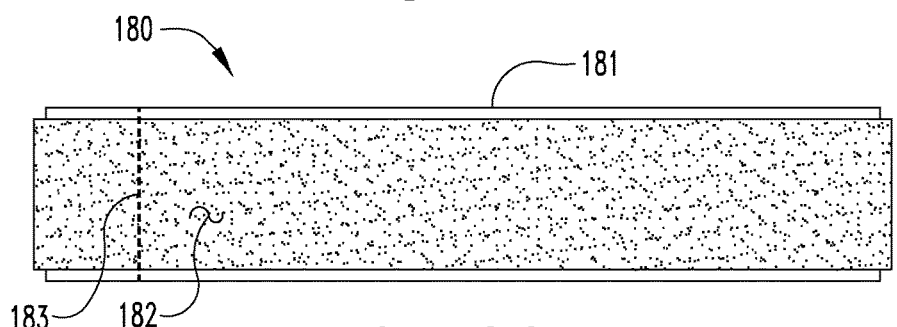
Fig. 38B

MEDICAL DEVICES AND METHODS USEFUL FOR APPLYING BOLSTER MATERIAL

REFERENCE TO RELATED APPLICATIONS

The present application is a continuation patent application of U.S. patent application Ser. No. 12/110,006, filed Apr. 25, 2008, entitled MEDICAL DEVICES AND METHODS USEFUL FOR APPLYING BOLSTER MATERIAL, which is a continuation patent application of U.S. patent application Ser. No. 11/060,078, filed Feb. 17, 2005, entitled MEDICAL DEVICES AND METHODS USEFUL FOR APPLYING BOLSTER MATERIAL, which is hereby incorporated by reference and which claims the benefit of U.S. Provisional Patent Application Ser. No. 60/545,513 filed Feb. 17, 2004, which is also hereby incorporated by reference.

BACKGROUND OF THE INVENTION

The present invention resides generally in the field of medicine and in particular aspects to devices and methods that are useful for applying a bolster material to a device for inserting surgical fasteners, e.g. a surgical stapler.

As further background, surgical stapler devices are designed to seal or simultaneously cut and seal an extended segment of tissue in a patient. Some surgical staplers include two stapler arms, a first arm including two or more lines of multiple staples (also called a "cartridge" or "jaw") and a second arm including an anvil or other feature adapted to bend each of the staples into a closed position upon operation of the stapler. So-called "anastomotic" staplers include a surgical blade in the device to sever tissue between the lines of staples. Those without such a cutting blade have been referred to as "non-anastomotic" staplers.

For some medical procedures, the use of bare staples, with the staples in direct contact with the patient's tissue, is generally acceptable. The integrity of the patient's tissue itself will normally serve to prevent the staples from tearing out of the tissue and compromising the seam before healing has occurred. However, in other procedures, the patient's tissue to be sealed is too fragile to securely hold the staples in place. For example, in the case of lung tissue, and in particular diseased lung tissue, the tissue to be stapled is fragile and, in extreme cases, will easily tear through unprotected staple lines. With the growing use of surgical staplers in operations on diseased lung tissues such as bullectomies and volume reduction procedures, it has become increasingly important to take measures to protect fragile tissue from tissue tears due to surgical staples or surgical stapling procedures.

One known protective measure involves the use of a reinforcement or bolster material, wherein the staples are inserted both through the bolster material and the patient's tissue. In many cases, as a preliminary step, the reinforcement material is in some manner applied to the arms of the surgical stapler, e.g. with portions applied to each arm, and the stapler thereafter used to secure tissue of the patient. The present invention provides medical devices and methods that are useful for applying bolster material to surgical staplers or other similar surgical fastening devices.

SUMMARY OF THE INVENTION

In one aspect, the present invention provides a medical device useful for applying a bolster material to a surgical stapler or other similar surgical fastening device, wherein the medical device includes an applicator element and a bolster material coupled to one another. This coupling can, for instance, be of such a nature that the bolster material and the applicator element are retained in association with one another without other mechanical components.

In one embodiment, the present invention provides a medical device useful for applying a bolster material to a surgical fastening device having a first arm and a second arm presenting respective first and second opposed surfaces. The medical device of the invention includes an applicator element having at least a first side, and one or more pieces of bolster material coupled to the applicator element and presented at the first side of the applicator element. The bolster material can be coupled to the applicator element, for example, by portion(s) of the bolster material extending through and/or around the applicator element, and/or by bonding. The bolster material presented at the first side of the applicator element can be brought into contact with a first arm surface of the fastening device during a loading procedure. In certain embodiments, bolster material is presented at both first and second sides of the applicator element, for application to both first and second arm surfaces of the fastening device. Illustratively, the opposed arm surfaces of a device such as a surgical stapler can be closed around a medical device of the invention so as to cause adherent contact of the arm surfaces with the bolster material. The coupling between the bolster material and the applicator element can be eliminated, so that the applicator element can be separated from the bolster material contacting the arm surfaces, to leave bolster material on the surfaces when the arms are separated. The applicator element can then, if desired, be disposed of. Additional embodiments of the invention relate to methods of manufacture and of use of devices such as those described above, as well as inventive applicator elements and bolster material constructs used in such devices.

In another embodiment, the invention provides a bolster device that includes a bolster material configured for application to an arm of a surgical fastening device, and a dried, reversible adhesive coating on said bolster material.

In still another embodiment, the invention provide a medical device, for example a bolster device, that includes a layer of dried, collagenous extracellular matrix (ECM) material, and a dried, reversible adhesive coating on the layer of ECM material.

Additional embodiments as well as features and advantages of the invention will be apparent from the further descriptions herein.

DESCRIPTION OF THE FIGURES

FIG. 1 provides a front view of an applicator element of the invention.

FIG. 2 provides a front view of a bolster material construct of the invention.

FIG. 3 provides a front view of a medical device of the invention including the applicator element and bolster material construct of FIGS. 1 and 2, respectively.

FIG. 4 provides a right end view of the medical device of FIG. 3.

FIG. 5 provides a front view of another applicator element of and for use in the invention.

FIG. 6 provides a front view of another medical device of the invention useful for applying a bolster material.

FIG. 7 provides a cross-sectional view of the device of FIG. 6.

FIGS. 8-11 provide front views of additional medical devices (FIGS. 8 and 11) of the invention and bolster material constructs (FIGS. 9 and 10) that can be incorporated therein.

FIGS. 15-17 provide front views of another medical device of the invention (FIG. 17) and applicator element (FIG. 15) and bolster material construct (FIG. 16) components thereof.

FIGS. 28-30 illustrate another medical device of the invention and components thereof. FIGS. 28 and 30 provide front views of an applicator element and bolster material constructs, respectively. FIG. 29A provides a front view of a medical device assembled from the components of FIGS. 28 and 30. FIG. 29B provides a rear view of the device of FIG. 29A.

FIGS. 31-33 illustrate another medical device of the invention and components thereof. FIGS. 31 and 33 provide front views of an applicator element and bolster material constructs, respectively. FIG. 32A provides a front view of a medical device assembled from the components of FIGS. 31 and 33. FIG. 32B provides a rear view of the device of FIG. 32A.

FIGS. 36-38B illustrate another medical device of the invention and components thereof. FIGS. 36 and 37 provide side views of a bolster material loop and applicator element, respectively. FIGS. 38A and 38B provide side and front views, respectively, of a medical device assembled from the components depicted in FIGS. 36 and 37.

FIGS. 39-42 illustrate another medical device of the invention and components thereof.

DETAILED DESCRIPTION

Figures 12, 13, 14:
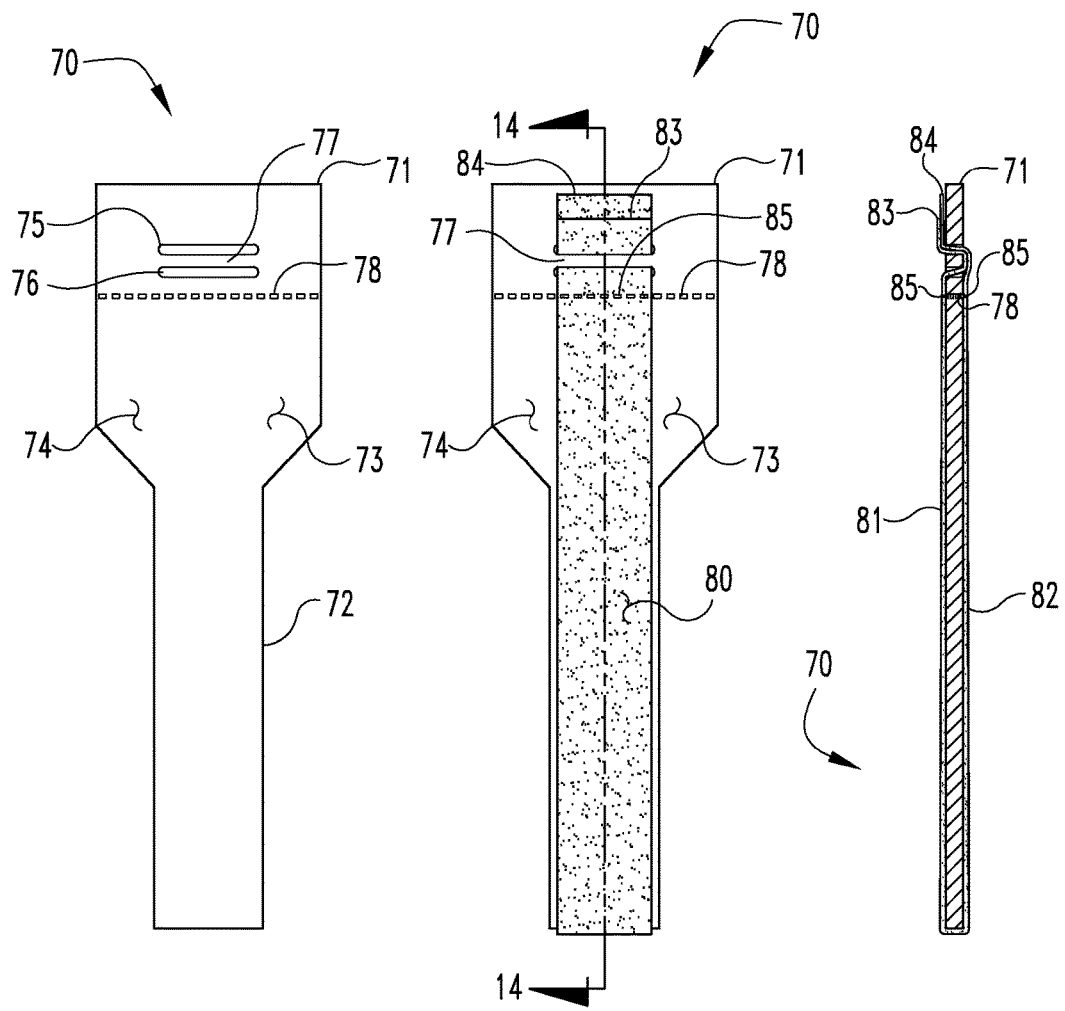
FIG. 12 provides a front view of another applicator element of the invention.
FIG. 13 provides a front view of another medical device of the invention incorporating the applicator element of FIG. 12.
FIG. 14 provides a cross-sectional view of the device of FIG. 13 taken along line 14-14 and viewed in the direction of the arrows.

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides medical articles useful for applying a bolster material to a surgical fastening device such as a surgical stapler, and related methods. In this regard, aspects of the present invention are at times described herein in connection with a surgical stapling device. While this represents an embodiment of the invention, it will be understood that the bolstering devices of the invention may be used in conjunction with a variety of surgical fastening devices that insert fasteners of various designs, including for example one-part and multiple (e.g. two) part staples, tacks, or other penetrating fasteners where bolstering may provide a benefit.

With reference now to FIG. 1, shown as a plan view of an applicator element 11 of and useful in the present invention. Applicator element 11 includes a body 12 to be used in conjunction with a staple bolster material. Body 12 is desirably formed all or in part of a compressible material, for example a polymer foam. Body 12 may, for example, be made from Styrofoam or another similar material. It will be understood, however, that body 12 can be made of any suitable material.

The illustrated body 12 generally includes a first rectangular portion 13 for accommodating a strip of staple bolster material, the rectangular portion 13 terminating in a generally wider portion including a first laterally extending portion 14 and a second laterally extending portion 15. Laterally extending portions 14 and 15 can, for instance, provide a segment of material that will extend laterally from the arms of a surgical stapler closed around applicator element 11. In this fashion, a user may grip portions 14 and 15 before and during the loading procedure. Lateral portion 14 is defined by first edge portion 16 extending transversely from the outside edge of generally rectangular portion 13. Edge 16 may form an angle greater than, less than, or equal to 90° relative to the outer edge of rectangular portion 13. Desirably, as illustrated, edge 16 forms a generally obtuse angle relative to the outer edge of rectangular portion 13. Lateral portion 14 is bounded by outer edge 17 which, as shown, is generally parallel the outer edge of the rectangular portion 13, although any other suitable relationship is contemplated. Lateral element 14 as illustrated also includes a third edge 18 which as shown is generally perpendicular to the outer edge of rectangular portion 13. The illustrated applicator element 11 includes a corresponding and opposed lateral element 15 defined by edge 19, 20, and 21 that are similar to edges 16, 17, and 18, respectively. It will be understood that in embodiments of the present invention including lateral extensions, the configuration of the lateral extension may take any form suitable to provide a segment to provide a user grip. For example, lateral extensions may be formed as generally triangular sections, rectangular sections, or circular segments, e.g. semi-circular portions, extending laterally of the rectangular portion 13. Applicator element 11 also includes an engaging end 22 for engaging a staple bolster material. Engaging end 22 desirably forms a shoulder at an intersection with a wider portion of applicator element 11, for example including a width W1 generally less than that of the adjacent portion including lateral extensions 14 and 15, optionally with width W1 being less than or about equal to width W2 of the rectangular portion 13, although this is not necessary to the broader aspects of the present invention.

With reference now to FIG. 2, shown is an inventive strip of staple bolster material 23 that can be used in conjunction with applicator element 11 of FIG. 1. Staple bolster strip 23 includes a generally elongate body 24 having a first opening 25 and a second opening 26 defined adjacent opposed ends thereof. Openings 25 and 26 can be of any suitable size and dimension, including slits, apertures, or other openings suitable for use in conjunction with cooperating engaging portions of applicator elements. Staple bolster strip 23 as shown is generally rectangular in its external shape including first elongate edge 27, second elongate edge 28, and end edges 29 and 30 extending generally perpendicular thereto. Staple bolster strip 23 can be made from any suitable material to bolster a staple line or single staple, including those materials described hereinbelow.

With reference now to FIG. 3, shown is an assembled medical device 31 useful for applying a staple bolster material to a surgical stapler, having staple bolster strip 23 coupled to applicator element 11. In particular, in one mode of assembly, engaging portion 22 of applicator element 11 can be inserted through aperture 26 adjacent to end 30 of the staple bolster strip 23. Staple bolster strip 23 can then be extended down and around generally rectangular portion 13 so as to encompass both sides thereof. Applicator element 11 can then be deformed as necessary to insert the engaging portion 22 through aperture 25 adjacent end 29. This will provide an arrangement as illustrated, in which the staple bolster strip 23 is wrapped around element 11 and secured thereto with the help of engaging portion 22 which extends through apertures 25 and 26 of staple bolster strip 23. With reference to FIG. 4, shown is a right-end view of the medical device 31 of FIG. 3. As shown, staple bolster strip 23 is wrapped around applicator element 11, with the engaging portion 22 extending through apertures 25 and 26.

Figure 44:
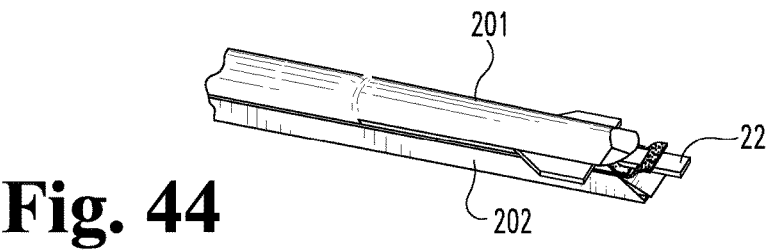
Figure 45:
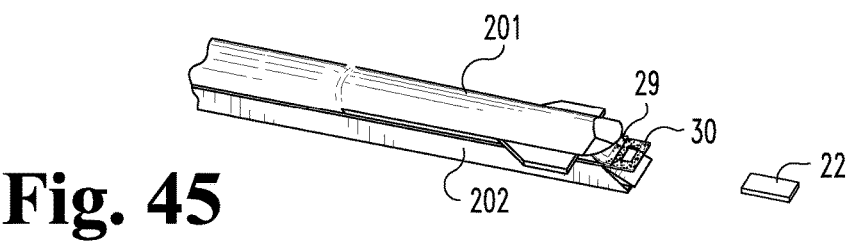
Figure 46:
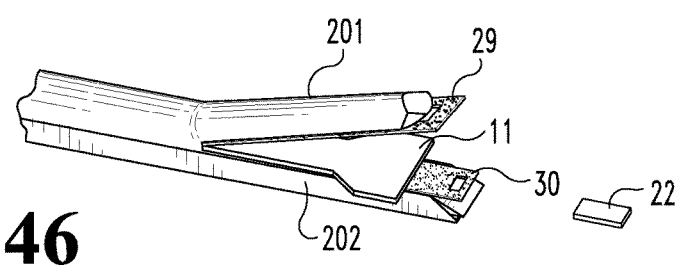
Figure 47:
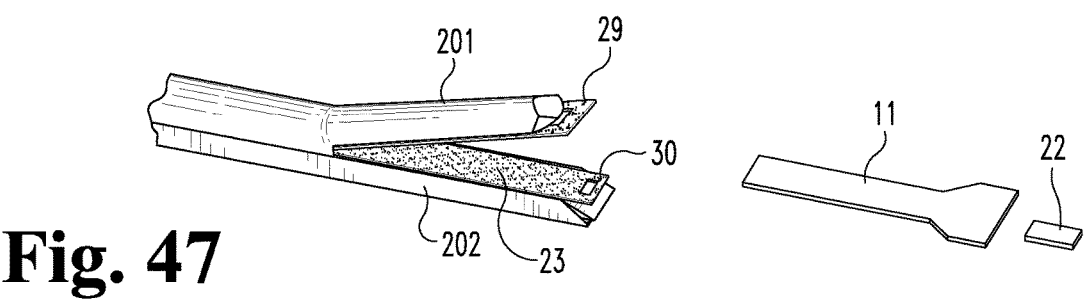

With reference now to FIGS. 1-4 together with FIGS. 43-47, an illustrative manner of using the medical device 31 in conjunction with a surgical stapler 200 will be described. With the arms 201 and 202 of the surgical stapler in an open condition (see FIG. 43), the assembled medical device 31 can be inserted between the arms of the surgical stapler 200 so as to align the staple bolster strip 23 with the opposed surfaces of the respective arms. The arms are closed around the medical device 31 so as to bring the opposed surfaces in contact with the staple bolster strip 23 on opposite sides thereof, as shown in FIG. 44. Staple bolster strip 23 is caused to adhere to the stapler arm surfaces, optionally with the assistance of a sticking agent. With the arms in the closed condition, the engaging portion 22 can be separated from the remainder of the applicator element 11 so as to cause a release of the ends 29 and 30 of the staple bolster strip 23, as shown in FIG. 45. As examples, the separation of the engaging portion 22 can be caused by tearing or cutting. After the separation of the engaging portion and release of the staple bolster ends 29 and 30, the arms 201 and 202 are caused to separate, whereupon staple bolster strip 23 remains adhered to and is carried apart by the arm surfaces generally forming a "V" configuration conforming to that provided by the arm surfaces. In this state, the major portion of the applicator element will remain between the arms 201 and 202 along with the staple bolster strip 23, as illustrated in FIG. 46. Applicator element 11 can then be removed from the surgical stapling device, leaving staple bolster strip 23 associated with the staple bolster device for use in reinforcing one or more staples to be implanted using the surgical stapling device 200. With reference generally to the above discussion, in another mode of use, the engaging portion 22 can be deformed or otherwise manipulated so as to be removed from the apertures 25 and 26 to disengage the ends 29 and 30 from the applicator element 11. Otherwise, the application procedure can be the same.

With reference to FIG. 5, shown is an alternative applicator element 11A for use in medical devices of the invention. Applicator element 11A is similar to applicator element 11 described above, except having a weakened portion 32 to facilitate a tear-away operation to remove engaging portion 22 and thereby release ends 29 and 30 of an associated staple bolster strip 23. Weakened portion 32 may include any suitable means for facilitating tearing or breaking along the area, including for example perforations, scores, thinner portions, and the like. These and other adaptations for facilitating separation of the engaging portion 22 will be recognized by the skilled artisan and are encompassed by the present invention. Further, applicator element 11A (as well as applicator element 11) may have a slit or cut lines 33 and 34 provided at the intersection of lateral portions 14 and 15 and generally rectangular portion 13, forming "dog ears" 35 and 36 which can be folded up and/or down (including both up, both down, or one up and one down) to provide laterally-positioned nibs or similar members for limiting side-to-side sliding of bolster material (e.g. strip 23) associated with the applicator element. In addition or alternatively, the end of rectangular portion 13 on applicator elements 11,11A can be notched (e.g. by cutting along line 37) to leave lateral pieces 38 and 39. With bolster strip 23 received around such end and within the notch, lateral pieces 38 and 39 can serve to limit side-to-side sliding of the bolster material. It will be understood that a similar end-notching approach could be used on both ends of applicator elements 11,11A and at one or both ends of other overall applicator element shapes, including those disclosed herein.

With reference to FIG. 6, shown is another medical device 40 of the invention that is useful for loading a staple bolster material on a surgical stapling device. Medical device 40 includes an applicator element 41 that has a generally rectangular portion 42 terminating in a wider portion including a first laterally extending portion 43 and a second laterally extending portion 44, similar to those found in applicator element 11 of FIG. 1. Applicator element 41, however, is devoid of the engaging portion 22 shown for applicator element 11 of FIG. 1. Instead, applicator element 41 terminates in a generally straight edge connecting the outer edges of lateral portions 43 and 44. A strip of staple bolster material 45 is associated upon applicator element 41. In the illustrated device, this is accomplished by looping the strip 45 around the applicator element 41, and adhering juxtaposed surfaces of the strip to one another in the area 46 so as to stably engage staple bolster strip 45 around application element 41. This adherence can be achieved by any suitable means, including bonding agents, cross-linking, glues, or other substances or mechanisms. Device 40 may also include a weakened, tearable portion 47 provided in the bolster material, for example, by perforations, score marks, thinner wall sections, or the like, as discussed above.

FIG. 7 provides a cross-sectional view of device 40 showing staple bolster strip 45 looped completely around and secured to applicator element 41, with the opposed segments of the bolster strip 45 adhered to one another in the area 46. In use, medical article 40 can be gripped either in area 46 or by lateral portions 43 and/or 44, and inserted between the arms of a surgical stapling device as generally discussed above. The arms can be closed around device 40, and the bolster strip 45 can be torn along line 47 so as to create two free ends of the bolster material 45. The arms of the stapling device can then be separated thereby carrying with them respective segments of the staple bolster material 45, and applicator element 41 removed to leave the loaded surgical stapler.

With reference now to FIG. 8, shown is another medical device 50 of the invention useful for applying a staple bolster material to the surgical stapler. Medical device 50 includes an applicator element 51 similar to element 41 described above, including a generally rectangular portion 52, and lateral portions 53 and 54. Medical device 50 includes a staple bolster strip 55 wrapped around applicator element 51 and secured thereupon. With reference to FIGS. 8 and 9 together, staple bolster strip 55 is secured around applicator element 51 with a slot and tab combination. In particular, staple bolster strip 55 includes a slot 56, and a tab 57 connected to the main body of strip 55 by a relatively narrower portion 58. In use, strip 55 is secured around applicator element 51 by folding or otherwise deforming and inserting tab 57 through slot 56, so as to create a secure loop of material around applicator element 51. In use, device 50 can be grasped by a user at lateral portions 53 and/or 54, and/or in areas of the strip 55 extending beyond applicator element 51, e.g. near tab 57. Thus grasped, device 50 can be inserted between arms of a stapler generally as discussed above, the arms closed around device 50, and tab 57 pushed back through slot 56 so as to release the strip 55 from the applicator element 51. Thereafter, the arms can be separated and applicator element 51 removed to leave the loaded surgical stapler device. Alternatively, the staple bolster strip 55 can be torn, for example in areas occurring adjacent slot 56 and in narrower portion 58, to release the staple bolster strip 55 from the applicator element 51. This tearing operation can occur while the arms are closed around device 50. Thereafter, the arms can be separated, the applicator removed, thus again leaving the loaded surgical stapler.

Further in this regard, shown in FIG. 10 is an alternative staple bolster strip 55A including an aperture 56A and a tab 57A similar to those in strip 55 shown in FIG. 9. However, staple bolster strip 55A also includes weakened portions such as perforations 59A and 59B occurring adjacent slot 56A and tab 57A, respectively. These perforations or other weakened portions can serve to provide a location for more predictably separating strip 55A to release the same from the applicator element in operations such as those discussed above.

With reference now to FIG. 11, shown is another medical device 60 of the invention. Device 60 is similar to device 50 shown in FIG. 8, except applicator element 61 lacks the lateral portions found on element 51. Thus, device 60 includes a generally rectangular applicator element 61 having a first end 62 and a second end 63 around which the staple bolster strip 55 (or 55A) can be secured.

FIGS. 12-14 illustrate another medical device 70 of the invention. Shown in FIG. 12 is applicator element 71 including a generally rectangular portion 72 terminating in a generally wider portion providing laterally extending portions 73 and 74. Applicator 71 includes slots 75 and 76 which are useful for receiving and securing a staple bolster strip. Slots 75 and 76 are separated by an intermediate portion 77. With reference now especially to FIGS. 13 and 14, medical device 70 includes a staple bolster strip 80 wrapped around and secured by applicator element 71. In particular, the strip 80 is wrapped around the lower end of element 71 and is secured to applicator element using slots 75 and 76. As shown, this can be achieved by threading a segment 81 of bolster strip 80 (front segment, FIG. 13) through aperture 76, around intermediate portion 77, and back through aperture 75. Another segment 82 of bolster strip 80 can be threaded overtop segment 81 and through aperture 75. In this manner, the end 83 of segment 81 and the end 84 of segment 82 will both occur on the same side of element 71 (front side, as illustrated) and the bolster strip 80 will thereby be secured to the applicator element 71 in somewhat of a "belt buckle" fashion. In use, the device 70 can be compressed between arms of a surgical stapler as described for devices hereinabove, to bring the bolster strip 80 into adherent contact with the opposed arm surfaces. Thereafter, the ends 83 and 84 of bolster strip 80 can be manually forced out of engagement with apertures 75 and 76, and the arms separated and the applicator element 71 removed. Alternatively, with continuing light compression between the arms, the applicator element 71 may be slipped from in between the arms, thus leaving in place the bolster strip 80. Still further, with continuing reference to FIGS. 12-14, applicator element 71 can be provided with perforations, a score, or another weakened area 78, and/or bolster strip 80 can be provided with similar weakened areas 85, such that while compressed between the arms, the applicator element 71 and/or bolster material 80 can be separated (e.g. torn) along the weakened area to disengage the bolster strip 80 from the element 71, whereafter the arms can be separated and the remainder of element 71 removed to provide the loaded stapling device.

FIGS. 15-17 illustrate another medical device 90 of the invention. Device 90 includes an applicator element 91 having a generally rectangular portion 92 and a pair of slits 93 and 94 therein. Slits 93 and 94 extend inwardly from opposed sides of applicator element 91, and extend partially across its width. Staple bolster strip 95 includes a central portion 96, a first leg 97 and a second leg 98. As illustrated, bolster strip 95 can be wrapped around applicator element 91, and each leg 97 and 98 threaded through its corresponding slit 93 and 94 to the opposite side of the element 91. In this fashion, bolster strip 95 can be held in association with applicator element 91. Device 90 can be used in fashions similar to those described for device 70 above, including for example the provision of appropriate weakened portions on the applicator element 91 and/or bolster strip 95 for a separation feature.

Figure 18:
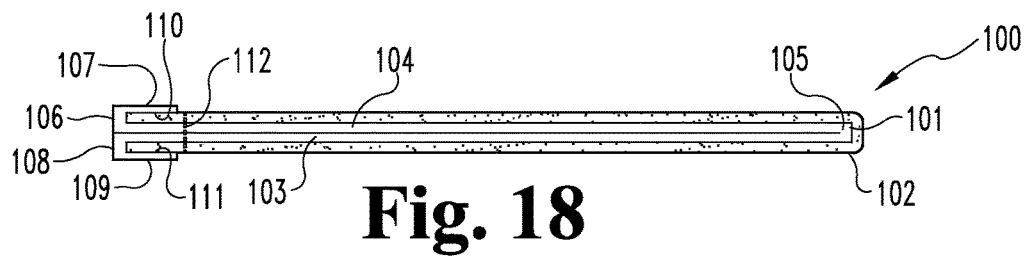
FIGS. 18-19 a side view and a front view of another medical device of the invention, respectively.
Figure 19:
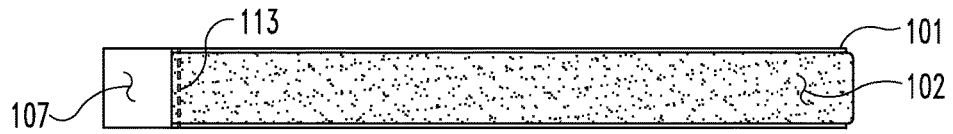

With reference to FIGS. 18 and 19, shown is still another embodiment to the invention. Shown is device 100 including an applicator element 101 and associated therewith a bolster strip 102. Applicator element 101 is a dual-layer element including layers 103 and 104, which can be created for example by folding a single piece, e.g. at fold line 105. The applicator element 101 includes a leg 106 extending transversely from layer 104 and a leg 107 extending transversely from leg 106. Corresponding structures 108 and 109 extend from layer 103. In this fashion, a "U"-shaped pocket is created for receiving end portions 110 and 111 of bolster strip 102 to facilitate holding bolster strip 102 in association with applicator element when wrapped therearound. As with other devices described herein, the applicator element 101 can optionally include a weakened portion 112, and/or the bolster strip 102 can optionally include a weakened portion 113.

Figure 20:
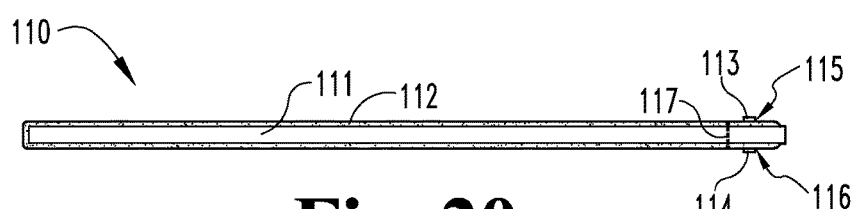
FIGS. 20-21 provide a side view and a front view of view of another medical device of the invention, respectively.
Figure 21:
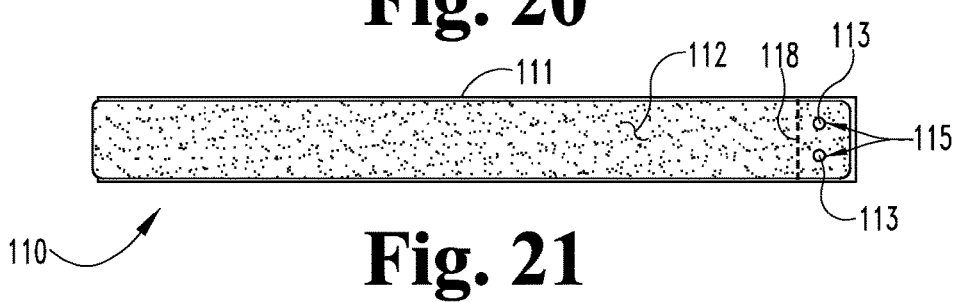

FIGS. 20 and 21 illustrate another embodiment of the invention. Shown is device 110 including applicator element 111 and a strip of bolster material 112. Again, bolster strip 112 is generally wrapped around element 111. In device 110, bolster strip 112 is held in association with element 111 through the use of raised pegs 113 and 114 of applicator element 111, which cooperate with corresponding apertures 115 and 116 in bolster strip 112. Pegs 113 and 114 fit snugly into apertures 115 and 116 thereby securing bolster strip 112 in association applicator element 111. Again, perforations or other weakened areas 117 and 118 can be provided in applicator element 111 and bolster strip 112, respectively.

Figure 22:
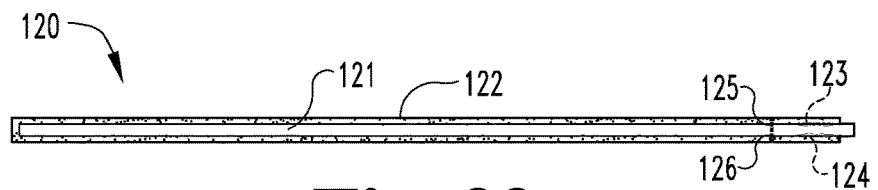
FIGS. 22 and 23 provide a side view and a front view of another medical device of the invention, respectively.
Figure 23:
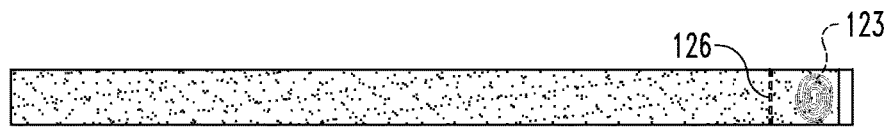

With reference now to FIGS. 22 and 23, shown is another embodiment of the invention, in which device 120 includes a generally rectangular applicator 121 and secured therearound a bolster strip 122. Bolster strip 122 is secured in association with applicator element 121 through the use of glue, adhesive, or another bonding agent in areas such as those found at 123 and 124 on each side of the applicator element 121. Perforations, scores, or other weakened areas 125 and 126 can be provided in the bolster strip 122 and applicator element 121, to facilitate a tear away or other separation operation as discussed above.

Figure 24:
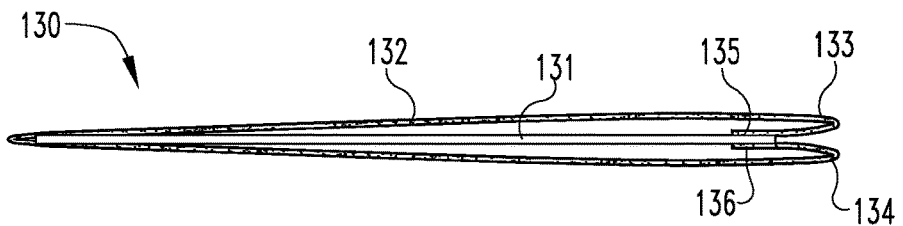
FIGS. 24 and 25 provide a side view and a front view of another medical device of the invention, respectively.
Figure 25:
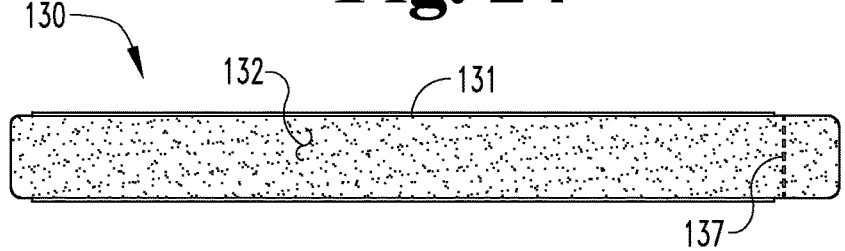

Shown in FIGS. 24 and 25 is another embodiment of the invention, in which device 130 includes applicator element 131 in a bolster strip 132. In the illustrated device 130, bolster strip 132 includes portions extending beyond element 131, which are folded back at locations 133 and 134, with the ends 135 and 136 of the bolster material 132 being secured to the applicator element 131 by any suitable bonding or other attachment method. Bolster strip 132 can be provided with a weakened area 137 extending through all layers of bolster material at that location. In this fashion, with the device 130 compressed between the arms of a surgical stapler, bolster strip 132 can be torn along line 137 so as to release two free ends thereof and disengage the bolster strip 132 from the applicator element 131. After the opposed arms are separated with bolster material 132 remaining in adherent contact therewith, both the portions of the bolster strip 132 torn away and those remaining attached to the applicator element 131 can be disposed, leaving the loaded stapling device. Alternatively, device 130 can lack any perforations or other weakened areas, for example when the bolster material is tearable in and of itself, or can be cut with a suitable instrument to loose the free ends as discussed above.

Figure 26:
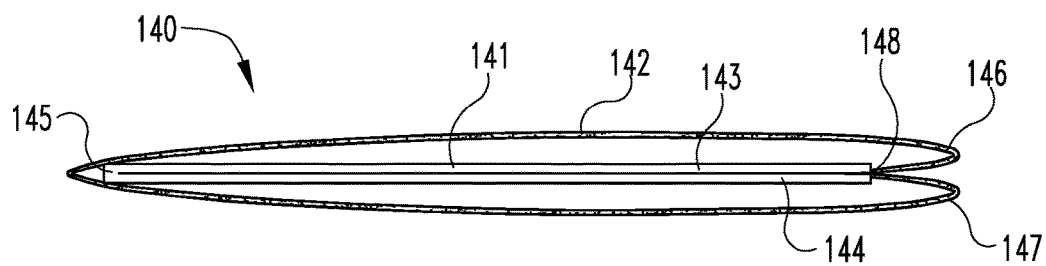
FIGS. 26 and 27 provide side and front views of another medical device of the invention, respectively.
Figure 27:
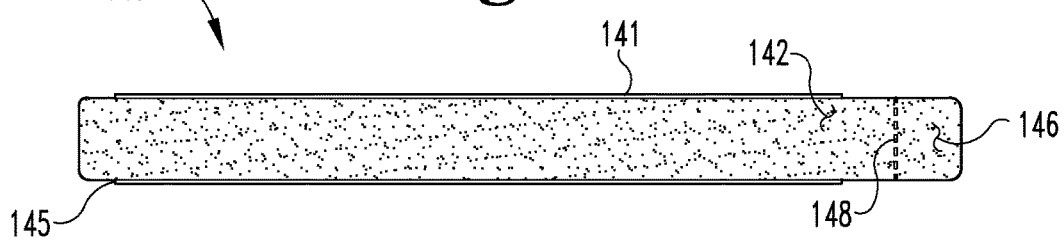

With reference to FIGS. 26 and 27, shown is another embodiment of the invention. Device 140 includes an applicator element 141 and its associated bolster strip 142. Applicator element 141 includes two layers 143 and 144, which can be formed by folding a single piece, e.g. at location 145. Bolster strip 142 in device 140 includes overhanging portions and fold lines 146 and 147, generally corresponding to features found in device 130 described above. However, in device 140, the ends of bolster strip 142 are not adhered to the outer surface of element 141, but are rather tucked in between the two layers thereof to secure the same. Suitable bonding or other attachment means can be used to facilitate retaining the ends of bolster strip 142 between the layers 143 and 144 can be used if desired or necessary. Bolster strip 142 can include a weakened area 148 extending through all layers at the location, to facilitate a tearing operation as described above. Alternatively, as discussed above, bolster strip 142 can lack any such weakened area if the bolster material is itself tearable or can be cut with a suitable instrument to provide free ends of bolster material and disengagement of the bolster material 142 from the applicator element 141.

FIGS. 28-30 show another embodiment of the invention. Device 150 includes an applicator element 151, a first piece of bolster material 152 and a second piece of bolster material 153. Applicator element 151 includes flaps 154, 155, 156, and 157 defined by adjacent slits in the material forming applicator element 151. Bolster pieces 152 and 153 include corresponding portions 154 prime, 155 prime, 156 prime, and 157 prime, which can have segments tucked behind flaps 154-157 so as to hold the bolster pieces 152 and 153 to opposed sides of applicator element 151, as shown. As in other embodiments, device 150 can optionally include score lines or other weakened areas providing tear lines in one or more of the applicator element and bolster pieces as represented by 158, 158a, and 158b. The device 150 is generally used as our devices discussed above to load the surfaces of a surgical stapler with the bolster material. In this regard, the portions 154', 155', 156', and 157', can be untucked prior to inserting a device between the stapler arms, if desired. Alternatively, applicator element 151 can be pulled out of the stapler while maintaining gentle compression on device 150 with the stapler arms, to leave bolster pieces 152 and 153 positioned on the stapler arms. For these purposes, the surface of the applicator element 151 can have a sufficiently low coefficient of friction for the applicator removal procedure while leaving the bolster material on the stapler arms, either provided by the material from which element 151 is made, or by relatively lower friction coatings or layers bonded thereto.

With reference to FIGS. 31-33, shown is another embodiment of the invention that is similar to that shown in FIGS. 28-30. However, device 160 of FIGS. 31-33 lacks lower end flaps corresponding to those of 156 and 157. In this matter, the leading ends of bolster pieces 162 and 163 for insertion into the stapler can either be uncoupled to applicator element 161, or can be coupled to the applicator element in other ways. Otherwise, device 160 has elements corresponding to those of device 150, including tucked portions 164' and 165', flaps 164 and 165, and optional tear lines denoted by 166, 166A, and 166B.

Figure 34:
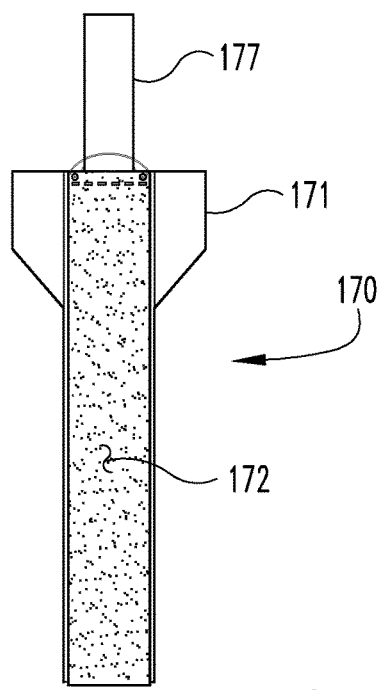
FIGS. 34 and 35 provide front views illustrating another medical device of the invention and components thereof.
Figure 35:
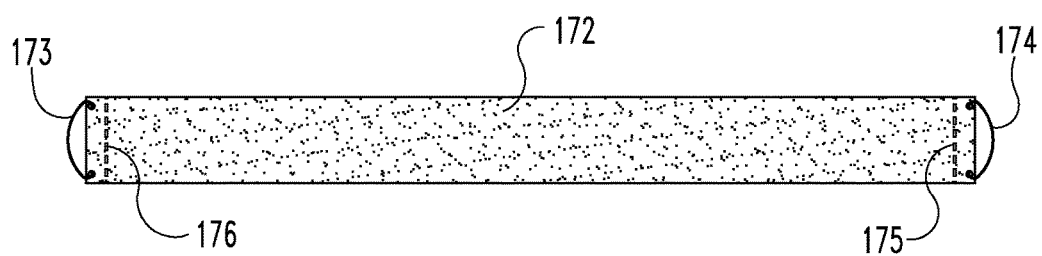
Figures 39, 40A, 40B:
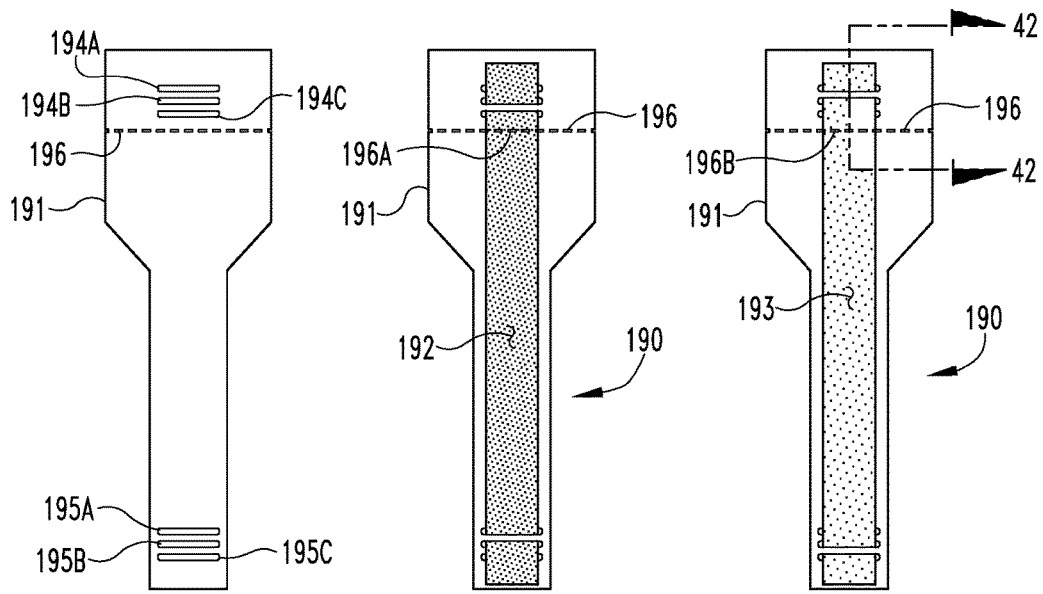
Figure 41:
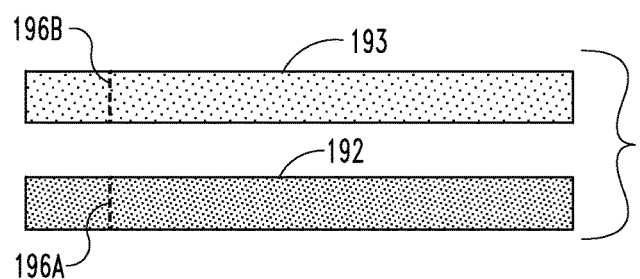

Another embodiment of the invention is shown in FIG. 34 and FIG. 35. In this embodiment, device 170 includes an applicator element 171 having features corresponding to those of applicator element 12 of FIG. 1. Device 170 includes a piece of bolster material 172 is provided, having loops 173 and 174 formed by suture material or any other suitable material attached near the ends of material 172. Bolster material 172 is coupled to applicator element 171 in a fashion analogous to that shown and described for device 31 of FIGS. 3 and 4, except attached loops 173 and 174 are received over engaging end 177 of applicator element 171. Also, perforation, score or other tear lines 175 and/or 176 can be provided adjacent ends of bolster piece 172 if desired. The use of device 170 can be analogous to that for device 31, with the user gripping and tearing away engaging portion 177 and optionally also loops 173 and 174; and, where tear lines 175 and 176 are incorporated, also tearing away end portions of bolster piece 172.

FIGS. 36-38B show another illustrative embodiment of the invention. Device 180 includes applicator element 181 in bolster material 182. Bolster material 182, as shown, is provided as a closed loop of material. In this regard, the bolster material may be manufactured or isolated as a tubular or closed loop material, or may be created from a sheet of material by forming the sheet into a loop and attaching the ends together, e.g. connected in either an end-to-end fashion or an overlapping fashion. When creating a loop out of an ECM or other collagenous material, the loop can be formed from a sheet that is looped and overlapped onto itself, with the overlapped regions bonded to one another. This bonding may be achieved all or in part by dehydrothermally bonding the layers together, for example under conditions of lyophilization as discussed elsewhere herein. Bolster material 182 in loop form is sized relative to applicator element 181 so that receipt of bolster material 182 around element 181 effectively holds the material 182 to the element 181. Illustratively, loop 182 can be received around element 181 under some level of tension retaining an effective association of the bolster material 182 with the applicator element 181. As in other embodiments, a tear line, represented at 183, can be provided through the bolster material and/or the applicator element, if desired.

Figure 42:
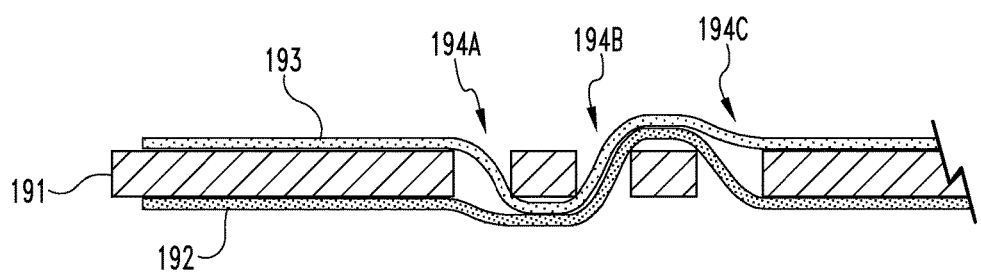
Figure 43:
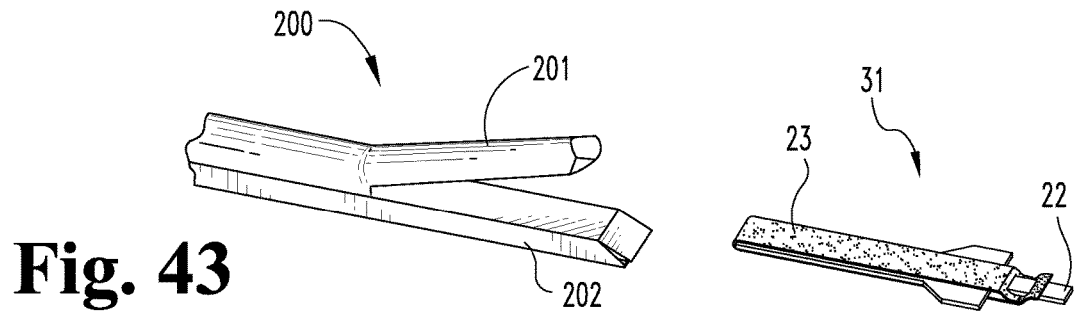
FIGS. 43-47 depict steps in an inventive method for applying a bolster material to a surgical stapler.

FIGS. 39-42 illustrate another embodiment of the invention, in which device 190 includes an applicator element 191 similar in many respects to element 71 of FIGS. 12-14. However, element 191 is adapted for more convenient receipt of separate bolster pieces on opposed sides of element 191. In this regard, a series of three (3) openings (e.g. slits or slots) 194A, 194B, and 194C are provided at a first end, and another series of three (3) openings 195A, 195B, and 195C, is provided at another end of element 191. Separate bolster pieces 192 and 193, which may be made of the same or different material from one another, are received on the applicator element 191. This is achieved in the illustrated embodiment by capturing each end of each bolster piece in the "belt buckle" fashion, as shown, by weaving the pieces through the openings. In the illustrative embodiment, this will involve overlapping portions of bolster pieces 192 and 193 as best shown in FIG. 42, which provides a cross-sectional view taken along line 42-42 of FIG. 40B and viewed in the direction of the arrows. It will be understood that if desired, overlapped portions of bolster pieces 192 and 193 could be avoided in a similar attachment mechanism by including one or more additional openings at each end of the applicator element 191 so that each end of pieces 192 and 193 could be woven through at least two slots unoccupied by the other. As other embodiments disclosed herein, optional score lines 196, 196A, and 196B can be provided in the applicator element 191 and/or bolster pieces 192 and 193. Again, as with other embodiments described herein, bolster pieces 192 and 193 could be disengaged from applicator element 191 prior to insertion between the stapler arms, and/or by an operation including gentle compression of device 190 between the stapler arms and sliding applicator element 191 out therefrom.

It will be understood that in medical devices of the invention, one piece, or more than one piece of staple bolster material, can be coupled to an applicator element, and bolster material may be presented at one or both sides of the applicator element. For example, separate pieces of staple bolster material can be presented on the separate sides of the applicator element as in some of the illustrated embodiments. Each piece of bolster material can be held in association with the applicator element using any of the disclosed features, for example being bonded to or retained by the applicator element by having a least a portion thereof received around, through, over, etc., the applicator element. All such embodiments are contemplated as a part of the present invention. Advantageously, although not necessary to the broader aspects of the invention, in certain embodiments, the bolster material will be retained in association with the applicator element without the use of any other mechanical component (e.g. a clip) compressing or otherwise holding the bolster material in contact with the applicator element. Thus, a bolster applicator device consisting of, or consisting essentially of, the applicator element and bolster material may be presented between the arms of the surgical stapler for the bolster loading operation.

Turning now to a discussion of the bolster material, any suitable biocompatible material can be used in the broader aspects of the invention. Reconstituted or naturally-derived collagenous bolster materials are desirable, especially collagenous extracellular matrix materials, such as submucosa, renal capsule membrane, dura mater, pericardium, serosa, peritoneum, dermal collagen, or basement membrane. The preferred bolster materials of the invention will include submucosa, such as submucosa derived from a warm-blooded vertebrate. Mammalian submucosa materials retaining substantially their native cross-linking are preferred, although additionally crosslinked materials may also be used. In particular, extracellular matrix materials derived from animals raised for meat or other product production, e.g. pigs, cattle or sheep, will be advantageous. Porcine submucosa provides a particularly preferred material for use in the present invention.

The submucosa can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

When a submucosa or other ECM material having differing characteristic sides is used in the invention, it can be oriented upon the medical device with a specified side directed outward for contact with the arm(s) of the surgical fastening device. For example, in the case of small intestinal submucosa, the material may be oriented with either the luminal or abluminal side facing outwardly for contact with the arm(s) of the surgical fastening device.

As prepared, an extracellular matrix (ECM) material for use in the present invention may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plate forming units (PFU) per gram, more preferably less than about 5 PFU per gram. These and additional properties of submucosa tissue taught in U.S. Pat. No. 6,206,931 may be characteristic of the ECM material used in the present invention.

Although not preferred, other implantable materials that may be employed as staple bolster materials in the present invention include non-bioresorbable or bioresorbable synthetic polymer materials such as polytetrofluroethylene (PTFE, e.g. GORE-TEX material), nylon, polypropylene, polyurethane, silicone, DACRON polymer, polyglycolic acid (PGA), polylactic acid (PLA), polycaprolactone, or others.

When a collagenous material is used as a staple bolster material in the invention, it may be desirable to bond areas of the collagenous material to one another, for example in securing the bolster material around all or a portion of an associated applicator element. Glues or other bonding agents may be used for this purpose, as discussed above. In addition or alternatively, collagenous material layers can be dehydrothermally bonded to one another, for example by drying the layers in contact with one another, e.g. under compression. The drying operation can, for example, occur in a lyophilization (freeze drying) or vacuum pressing process.

In certain embodiments of the invention, the staple bolster material will have a thickness in the range of about 50 to about 1000 microns, more preferably about 100 to 600 microns, and most preferably about 100 to about 350 microns. The staple bolster material will desirably provide sufficient strength to effectively reinforce the staple(s), for example exhibiting a suture retention strength in the range of about 100 to about 1000 gram force, e.g. typically in the range of about 200 to about 600 gram force, each of these based upon 5-0 Prolene suture and a bite depth of 2 mm. If necessary or desired, a multilaminate staple bolster material can be used. For example, a plurality of (i.e. two or more) layers of collagenous material, for example submucosa-containing or other ECM material, can be bonded together to form a multilaminate structure useful as a staple bolster material. Illustratively, two, three, four, five, six, seven, or eight or more collagenous layers containing submucosal or other collagenous ECM materials can be bonded together to provide a multilaminate collagenous bolster material. In certain embodiments, two to six collagenous, submucosa-containing layers isolated from intestinal tissue of a warm-blooded vertebrate, particularly small intestinal tissue, are bonded together to provide the staple bolster material. Porcine-derived small intestinal tissue is preferred for this purpose. The layers of collagenous tissue can be bonded together in any suitable fashion, including dehydrothermal bonding under heated, non-heated or lyophilization conditions, using adhesives, glues or other bonding agents, cross-linking with chemical agents or radiation (including UV radiation), or any combination of these with each other or other suitable methods.

If needed, a sticking agent can be used to facilitate temporary adhesion of the staple bolster material to the arm surfaces. Any substance or means that increases the attachment of the bolster material to the arm surface can be used, so long as the attachment is not so permanent as to deleteriously interfere with release of the bolster material after the surgical stapler has been fired or otherwise actuated to insert the staple or staples. The substance can be inorganic, organic, natural or synthetic. In many cases, biocompatible surgical lubricants will suffice to improve this adhesion. Biocompatible adhesive materials, including pressure-sensitive adhesives, may also be used, including for example polyvinyl pyrrolidones, polyvinyl alcohols, polyvinyl acetates, vinyl acetate esters, starches, dextrins, acrylic resins, polyurethanes, styrene/butadiene radon copolymers, silicones, polyisobutylenes, polyisoprene polyvinyl ethyl ether and copolymers, blends or combinations thereof. The adhesive can be applied to the bolster reinforcement material at the point of use, or in a pre-applied configuration. In certain embodiments, a pre-applied adhesive can be covered with release paper or similar material to protect the adhesive layer during shipping and handling. The release paper can then be removed prior to use.

Another aspect of the present invention provides an implantable device useful as a staple bolster material. The implantable device includes a dried, bioresorbable (and preferably bioremodelable) material having coated thereon a relatively thin layer of a dried, reversible adhesive substance. The bioresorbable material is preferably a collagenous material, more preferably an ECM material as discussed hereinabove. Single or multilaminate ECM materials can be used, and multilaminate materials including submucosal collagen are most preferred.

In certain inventive embodiments, the dried, reversible adhesive layer is non-tacky in the dried state, but becomes tacky when wetted with water or an otherwise biocompatible aqueous solution such as saline. In this manner, a medical device containing the inventive implantable material, including but not limited to the medical devices disclosed hereinabove, can be packaged and shipped in a dried state, and then wetted at the point of use (e.g. by attending medical personnel) to render the implantable material tacky. In the case of staple bolster materials, the material can then be adhered to the surgical stapler to provide a buttress for a staple or staple line. Suitable reversible, water-activating adhesive substances include, for example, polyvinyl pyrrolidones, polyvinyl alcohols, polyvinyl acetates, vinyl acetate esters, starches, dextrins, dextrans, sugars such as glucose, dextrose, and sucrose, carboxymethyl cellulose, carboxy methyl ethyl cellulose, hyaluronic acid, alginates, polylactides, gelatin, casein, polyethylene glycol and other glycols, carbomer, glycerols or polymers, blends or combinations thereof. Adhesive coatings including dextran, and in particular dextran having an average molecular weight of about 70,000 or higher, are preferred. The adhesive coating is desirably applied as a relatively thin layer, for example at a level of about 1 mg/cm$^2$ to about 100 mg/cm$^2$ on the surface of the bolster material, although higher or lower levels may be used with a particular adhesive and/or bolster materials. In the case of dextran and similar polymers, a level of about 4 mg/cm$^2$ to about 12 mg/cm$^2$ is preferred, although again higher or lower levels may be used in a particular circumstance.

The medical devices of the present invention can be used to facilitate a variety of surgical procedures. Such procedures include but are not limited to various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastro-intestinal procedures), and as a tool in a variety of other surgical procedures (e.g., reproductive organ repair procedures, etc.). In this regard, the medical devices of the invention may be used in conjunction with operations on both humans and animals. Likewise, the medical devices of the invention may be used with either anastomotic staplers or non-anastomotic staplers, and may be adapted, sized and shaped in a variety of ways to accommodate given stapler devices.

The medical devices of the invention can be provided in sterile packaging suitable for medical products. Sterilization may be achieved, for example, by irradiation, ethylene oxide gas, or any other suitable sterilization technique, and the materials and other properties of the medical packaging will be selected accordingly.

All publications cited herein are hereby incorporated herein by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical device useful for applying a bolster material to a surgical fastening device having a first arm and a second arm presenting respective first arm and second arm surfaces, the medical device comprising:
   an applicator element which is receivable between the first and second arms, said applicator element having a first side and a second side, a length, a width, and a thickness;
   said length and said width each greater than said thickness;
   said width varying along said length of the applicator element;
   at least a first piece of bolster material coupled to the applicator element and presented at least at said first side of said applicator element for contact with at least said first arm surface; and
   at least a second piece of bolster material coupled to the applicator element and presented at least at said second side of said applicator element for contact with at least said second arm surface, said second piece of bolster material separate from said first piece of bolster material;
   wherein the applicator element comprises a compressible foam material.

2. The medical device of claim 1, wherein the first and second pieces of bolster material comprises collagen.

3. The medical device of claim 2, wherein the first and second pieces of bolster material comprises an extracellular matrix material.

4. The medical device of claim 3, wherein said extracellular matrix material comprises bovine pericardium.

5. The medical device of claim 1, wherein the length has a first portion having a first width and a second portion having a second width and said first portion of said applicator element is rectangular in shape.

6. The medical device of claim 1, wherein the length has a first portion having a first width and a second portion having a second width and said second width of said second portion includes first and second laterally extending portions.

7. The medical device of claim 6, wherein said first and second laterally extending portions are rectangular in shape.

8. The medical device of claim 1, wherein an end of said applicator element defines a notch.

9. The medical device of claim 1, comprising laterally-positioned members laterally outward from said first piece of bolster material on said first side of said applicator element;
   said laterally-positioned members for limiting side-to-side sliding of the first piece of bolster material associated with the applicator element and extending above a surface supporting said first piece of bolster material on said first side; and
   wherein said laterally-positioned members are formed of said compressible foam material.

10. The medical device of claim 9, wherein said applicator element has a leading edge and a trailing edge, said leading edge passing between said first and second arm surfaces before said trailing edge when the applicator element is inserted between said first and second arms of said surgical fastening device; and
    wherein a forward facing surface of said laterally-positioned members faces toward but spaced from said leading edge of said applicator element and a rearward facing surface of said laterally-positioned members faces away and spaced from said leading edge of said applicator element.

11. The medical device of claim 9, wherein said applicator element has a leading edge and a trailing edge, said leading edge passing between said first and second arm surfaces before said trailing edge when the applicator element is inserted between said first and second arms of said surgical fastening device; and
    wherein a rearward facing surface of said laterally-positioned members faces away from said leading edge of said applicator element and is spaced from said trailing edge.

12. The medical device of claim 1, comprising a first adhesive material on a surface of said first or second pieces of bolster material for adhering said first or second pieces of bolster material to said first or second arm surface.

13. The medical device of claim 1, wherein the compressible foam material providing said first side, said second side, said first portion, and said second portion.

14. The medical device of claim 1, wherein said applicator element has a first portion of said length having a first width and a second portion of said length having a second width;
    wherein said first and second pieces of bolster material have a width measured along the same direction as the width of said applicator element; and
    wherein said first width of said applicator element is less than said width of said first and second pieces of bolster material and said second width of said applicator element is greater than said width of said first and second pieces of bolster material.

15. A medical device useful for applying a bolster material to a surgical fastening device having a first arm and a second arm presenting respective first arm and second arm surfaces, the medical device comprising:
    an applicator element which is receivable between the first and second arms, said applicator element having a first side and a second side and a length extending from a first end to a second end; said first end or said second end defining a notch extending from the first side to said second side; and
    at least a first piece of bolster material coupled to the applicator element and presented at least at said first side of said applicator element for contact with at least said first arm surface;
    at least a second piece of bolster material coupled to the applicator element and presented at least at said second side of said applicator element for contact with at least said second arm surface, said second piece of bolster material separate from said first piece of bolster material;
    wherein said second side of said applicator element faces away from said first side of said applicator element; and
    wherein the applicator element comprises a compressible foam material.

16. The medical device of claim 15, wherein the first and second pieces of bolster material comprises collagen.

17. The medical device of claim 16, wherein the first and second pieces of bolster material comprises an extracellular matrix material.

18. The medical device of claim 17, wherein said extracellular matrix material comprises bovine pericardium.

19. The medical device of claim 15, wherein the compressible foam material providing said first side, said second side, said first end, and said second end.

20. The medical device of claim 15, wherein said first end passes between said first and second arm surfaces before said second end when the applicator element is inserted between said first and second arms of said surgical fastening device.

* * * * *